US00PP31792P3

(12) United States Plant Patent
Gray et al.

(10) Patent No.: US PP31,792 P3
(45) Date of Patent: May 26, 2020

(54) FLORIBUNDA ROSE PLANT NAMED 'GRAOSR'

(50) Latin Name: ***Rosa* hybrid**
Varietal Denomination: GRAosr

(71) Applicants: John Charles Gray, Highfields (AU); Sylvia Elizabeth Gray, Highfields (AU)

(72) Inventors: John Charles Gray, Highfields (AU); Sylvia Elizabeth Gray, Highfields (AU)

( * ) Notice: Subject to any disclaimer, the term of this patent is extended or adjusted under 35 U.S.C. 154(b) by 0 days.

(21) Appl. No.: 16/350,973

(22) Filed: Feb. 6, 2019

(65) Prior Publication Data

US 2019/0246532 P1 Aug. 8, 2019

Related U.S. Application Data

(60) Provisional application No. 62/626,780, filed on Feb. 6, 2018.

(51) Int. Cl.
*A01H 5/02* (2018.01)
*A01H 6/74* (2018.01)

(52) U.S. Cl.
USPC ..... Plt./142
CPC ..... *A01H 6/749* (2018.05)

(58) Field of Classification Search
USPC ..... Plt./142
See application file for complete search history.

*Primary Examiner* — Anne Marie Grunberg
(74) *Attorney, Agent, or Firm* — Samuel R. McCoy, Jr.

(57) ABSTRACT

'GRAosr' is a new and distinct *floribunda* type cultivar of *Rosa* hybrid plant which is characterized by the combination of an upright, bushy growth habit, nearly continuous flowering, with flowers that exhibit a distinct strong red with petals yellow at the base and with a silver white reverse, and the stability of these characteristics from generation to generation. The new cultivar is generally suited to landscape applications.

2 Drawing Sheets

Latin name of genus and species: The Latin name of the genus and species of the novel variety disclosed herein is *Rosa* hybrid.

Variety denomination: The inventive variety of *Rosa* hybrid disclosed herein has been given the variety denomination 'GRAosr'.

BACKGROUND OF THE INVENTION

Parentage: 'GRAosr' is a seedling selection which resulted from the controlled cross-pollination of an unnamed *Rosa* hybrid female breeding line and an unnamed *Rosa* hybrid male breeding line. Both parents, developed by the same inventor and never commercially released, exhibited traits deemed commercially significant and desirable.

After many years of trialing, the female parent was confirmed to possess a combination of desirable traits such as very strong fragrance and having flower color white, borne on a bushy plant growing to 1.2 m tall and wide. The male parent was selected for use in breeding after trialing confirmed the presence of a modern flower color. During the spring of 2014, the female parent was emasculated and was manually pollinated with pollen from the male parent. In autumn of 2015, seed was collected from hips produced by the female parent and a number of seedlings were grown to a mature size, including the claimed plant. These progeny were further evaluated for desirable traits such as black spot disease resistance and original flower color, and in January of 2016 the claimed plant was first observed. In January of 2017, after further evaluation for desirable traits, the claimed plant was deemed to be garden-worthy and suited to widespread cultivation. It was given the denomination 'GRAosr'.

Asexual Reproduction: Asexual propagation of 'GRAosr', by way of softwood stem cuttings, was first performed in May of 2016 at the inventor's nursery in Highfields, Australia. Through more than twelve subsequent generations, the unique features of this cultivar have proven to be stable and true to type.

SUMMARY OF THE INVENTION

The following characteristics have been repeatedly observed and represent the distinguishing characteristics of the new *Rosa* cultivar 'GRAosr'. These traits, in combination, distinguish 'GRAosr' as a new and distinct cultivar.

1. *Rosa* hybrid 'GRAosr' exhibits an upright growth habit; and
2. *Rosa* hybrid 'GRAosr' flowers exhibit a distinct strong red with petals yellow at the base and with a silver white reverse; and
3. *Rosa* hybrid 'GRAosr' exhibits nearly continuous flowering; and
4. *Rosa* hybrid 'GRAosr' exhibits a double flower type; and
5. *Rosa* hybrid 'GRAosr' exhibits flowers with a strong rose fragrance.

DETAILED BOTANICAL DESCRIPTION

Figure 1:
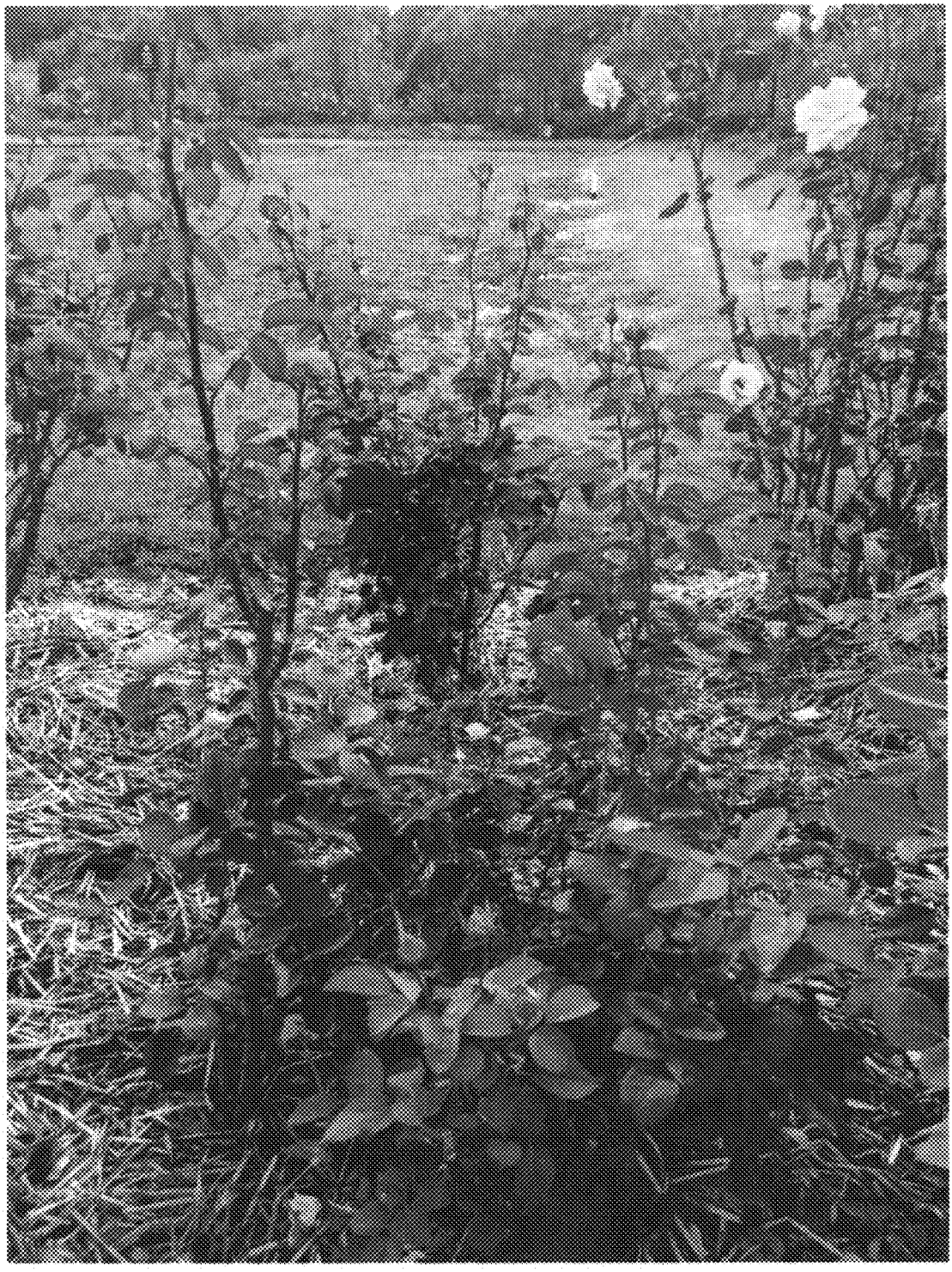
FIG. 1 illustrates, as nearly true as it is reasonably possible to make the same in color photographs of this type, an exemplary 6 month old 'GRAosr' plant grown outdoors at the inventor's commercial nursery in Highfields, Australia.
Figure 2:
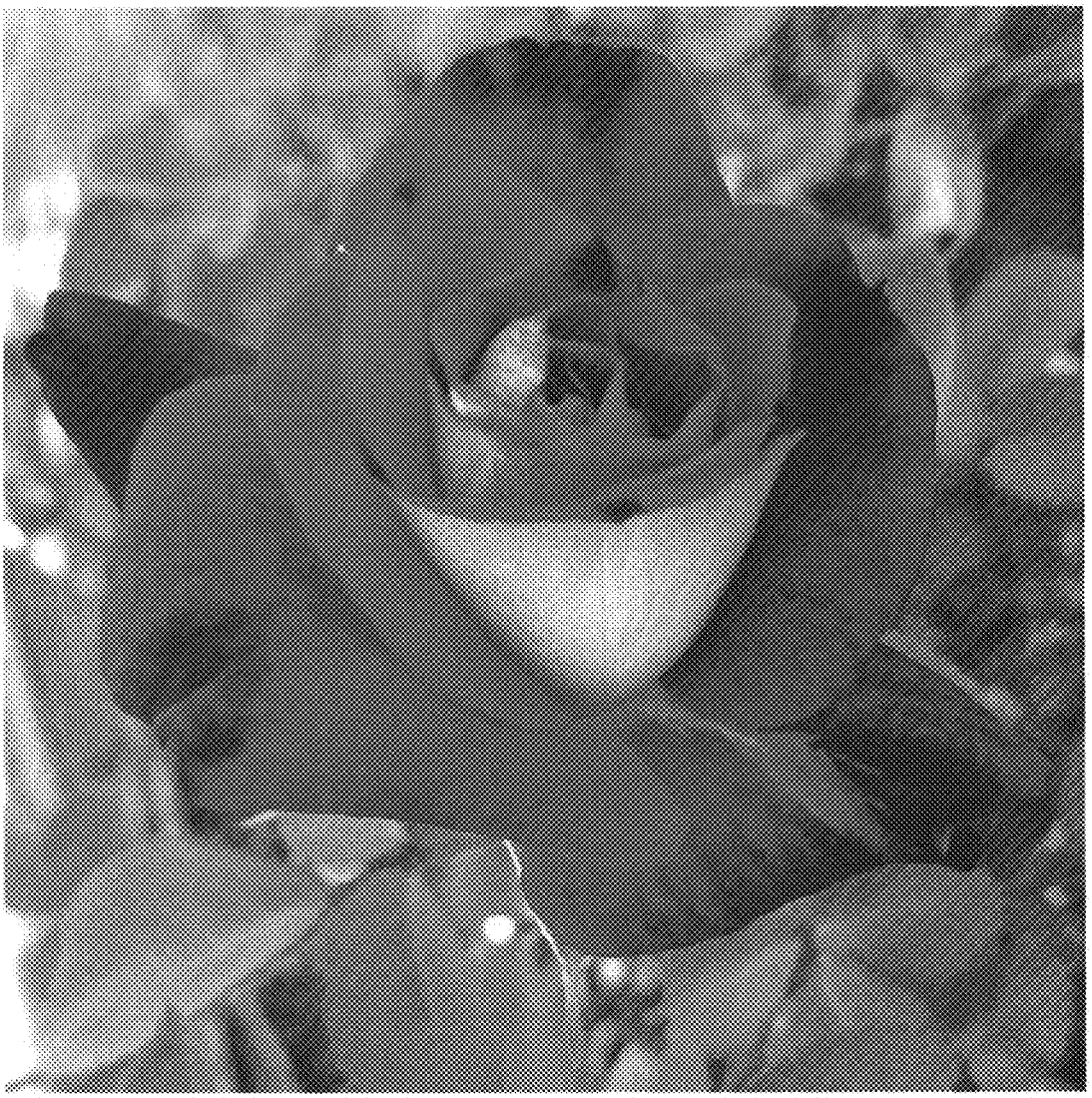
FIG. 2 illustrates, as nearly true as it is reasonably possible to make the same in color photographs of this type, the typical flower of 'GRAosr'.

The following observations and measurements, made in January of 2018, describe averages of two own-root specimens of one year old 'GRAosr' plants. The plants were grown outdoors in a garden bed of a red krasnozem soil in full sunlight, at the inventor's nursery in Highfields, Australia. No shade or supplemental light was provided. Temperatures ranged from approximately 17 to 35 degrees Celsius during the day and 7 to 18 degrees Celsius at night. Standard practices for irrigation, fertilizer and pest control were applied at appropriate times during the growing season. The plants were pruned three times during the growing season using accepted techniques for rose pruning.

Those skilled in the art will appreciate that certain characteristics will vary with older or, conversely, with younger plants. 'GRAosr' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2007 Fifth Edition except where common terms of color are used.

A botanical description of 'GRAosr' and comparisons with the parents and the most similar commercial cultivar of *Rosa* hybrid are provided below.

General plant description:

*Growth habit.*—Upright to semi-weeping.

*Growth rate.*—Approximately 6 months to reach 60 cm.

*Dimensions.*—60 cm tall and 50 cm wide.

*Environmental tolerance.*—Very good heat tolerance; cold hardiness is unknown.

*Disease resistance.*—Excellent resistance to powdery mildew (*Sphaerotheca pannosa*) and good resistance blackspot (*Diplocarpon rosae*).

*Propagation.*—Technique — Softwood stem cuttings. Time to initiate roots — About 13 days at approximately 21 degrees Celsius at root zone and 18 degrees Celsius ambient temperature. Time to produce a rooted cutting — About 25 days at approximately 21 degrees Celsius at root zone and 18 degrees Celsius ambient temperature.

Root system: White fibrous roots with many root hairs extending from lesser roots in a featherlike arrangement.

Branches:

*Branching habit.*—Irregular branching from mature branches, breaking first from the uppermost buds near the apex of each shoot.

*Quantity.*—Numerous.

*General dimensions.*—Approximately 70 cm long; 1.0 cm in diameter near the base and tapering to 0.4 cm.

*Immature branches.*—Diameter — Approximately 0.5 cm. Texture and pubescence — Smooth with prickles; glabrous. Color — Near RHS 145 with anthocyanin present. Prickles — Density — Sparse to moderate. Color — Near RHS 176D. Shape — Convex. Texture — Smooth.

*Mature branches.*—Diameter — Approximately 1.0 cm, after one year. Texture and pubescence — Smooth with prickles; glabrous. Color — Near RHS 144C.

*Prickles.*—Density — Sparse to moderate. Color — Near RHS 168C. Shape — Convex. Texture — Smooth.

Leaves:

*Arrangement.*—Alternate imparipinnate compound leaves.

*Quantity.*—Approximately 5 per mature branch.

*Attachment.*—Petiolate.

*Leaf internode length.*—4 cm.

*Dimensions.*—Approximately 8 cm long and 7 cm wide.

*Petiole.*—Dimensions — 3.0 cm long and 0.1 cm wide. Color — Near RHS 144C and margined RHS 144B. Texture and pubescence — Smooth and glabrous. Prickles — Present. Stipitate glands — Present.

*Stipule.*—Dimensions — 1.5 cm long and 0.5 cm wide. Color — Near RHS 144C. Texture and pubescence — Smooth and pubescent. Margins — Ciliate. Apex — Apiculate. Base — Winged. Prickles — Not present. Stipitate glands — Not present.

*Rachis.*—Dimensions — 1.3 cm long and 0.1 cm wide. Color — Near RHS N144A. Prickles — Not present. Stipitate glands — Not present.

*Leaflets.*—Quantity — Five leaflets on axillary leaves. Dimensions — Average size of the terminal leaflet is 5 cm long and 3 cm wide. Shape — Ovate. Apex — Acuminate. Base — Ovate. Margins — Serrated. Texture, pubescence and luster, adaxial surface — Smooth, glabrous, and glossy. Texture, pubescence and luster, abaxial surface — Smooth, glabrous, and matte. Juvenile foliage color, adaxial surface — Near RHS N137B, with no anthocyanin intonations. Juvenile foliage color, abaxial surface — Near RHS 138C, with anthocyanin intonations. Mature foliage color, adaxial surface — Near RHS 141B. Mature foliage color, abaxial surface — Near RHS 138B. Venation — Pinnate. Venation color, adaxial surface — Near RHS 141B, with midrib RHS 139D. Venation color, abaxial surface — Near RHS 139D, with midrib RHS N144B. Petiolule — Dimensions — 0.2 cm long and 0.1 cm wide. Color — Near RHS 141B with no anthocyanin intonations present. Prickles — Not present. Texture — Smooth.

Inflorescence:

*Inflorescence type.*—Flowers are clustered.

*Blooming habit.*—Almost continuous from October through June in the southern hemisphere.

*Time to flower.*—6 to 8 weeks for a new stem to mature and flowering begins to occur once a stem matures.

*Peduncle.*—Dimensions — 4.0 cm long and 0.2 cm in diameter. Color — Near RHS 53B. Strength — Rigid. Texture and pubescence — Smooth and pubescent. Prickles — Not present.

Bud:

*Shape.*—Ovate.

*Size.*—1.5 cm long and 1.0 cm in diameter.

*Color.*—Near RHS 142B with random anthocyanin.

Flower:

*Calyx.*—General — Comprised of five polysepalous sepals. Diameter of calyx — 0.5 cm. Sepals — Color, interior surface — RHS 150D. Color, exterior surface — RHS 142B with anthocyanin. Dimensions — 2.0 cm long and 0.7 cm wide. Apex — Apiculate. Base — Flat at union with receptacle. Quantity — Five. Pubescence — Densely puberulent. Margins — Entire. Stipitate glands — Not present.

*Corolla.*—General shape of corolla — Cupped with a tight outer whorl. Rate of opening — 6 days from bud to anthesis. Dimensions — Approximately 6 cm in diameter and 4 cm deep. Fragrance — Strong rose scent. Lastingness — On the plant for 5 days after anthesis. Persistence — Self-cleaning. Petals — Petal count — Exhibits double flowers with approximately 28 petals under normal conditions. Petal arrangement — Rounded whorl at anthesis and aging to a whorl. Dimensions — 3.1 cm long and 2.5 cm wide. Petal shape — Obovate. Apex — Rounded. Base — Flattened, then obtuse. Petal reflex — Slightly reflexed at apex. Petal margin — Entire; slightly undulating. Texture — Soft. Aspect — Formal. Petal color, upon opening — Upper surface — Near RHS 42A with base near 3A. Lower surface — Near RHS N155C with base near 33A. Petal color, at anthesis — Upper surface — Near RHS42A with base near 3A. Lower surface — Near RHS N155C with base near 33A. Fading — Near RHS N30A.

Reproductive organs:

*Stamens.*—Quantity — Approximately 50. Anthers — Shape — Narrow ovate. Length — 0.1 cm. Color — Near RHS 21B. Pollen — Many. Pollen Color — Near RHS 3A. Filaments — Color — Near RHS N25D. Length — Approximately 0.8 cm.

*Pistils.*—Quantity — Approximately 50. Length — Approximately 1.0 cm. Stigma — Shape — Ovate. Color — Near RHS 11B. Style — Length — Approximately 0.8 cm long. Color — Near RHS 18C.

*Ovary.*—Dimensions — 0.5 cm long and 0.3 cm wide. Color — Near RHS 3D.

*Receptacle.*—Shape — Pitcher-shaped. Dimensions — 0.5 cm high and 0.5 cm wide. Color — Near RHS 141D.

Hip and seed:

*Hip.*—Shape — Rounded. Dimensions — 1.0 cm long and 1.0 cm wide. Texture — Smooth. Color — Near RHS 142B.

*Seed.*—Shape — Rounded. Dimensions — 1.0 cm long and 1.0 cm wide. Color — Near RHS 144D.

COMPARISONS WITH THE PARENTS

The new rose plant 'GRAosr' may be distinguished from its seed parent, an unnamed breeding line, by the following combination of characteristics:

1. The flowers of 'GRAosr' exhibit a distinct strong red with petals yellow at the base and with a silver white reverse, whereas the flowers of the seed parent exhibit a white tonality.
2. 'GRAosr' exhibits an upright growth habit, whereas the seed parent exhibits an upright semi-weeping growth habit.

The new rose plant 'GRAosr' may be distinguished from its pollen parent, an unnamed breeding line, by the following combination of characteristics:

1. The flowers of 'GRAosr' exhibit a distinct strong red petals with yellow at the base and a silvered white reverse, whereas the flowers of the pollen parent exhibit a red general tonality.
2. 'GRAosr' exhibits a medium upright habit, whereas the pollen parent exhibits a tall upright growth habit.

COMPARISONS WITH THE MOST SIMILAR VARIETY OF COMMON KNOWLEDGE

Plants of the new cultivar 'GRAosr' may be distinguished from the commercial variety *Rosa* hybrid 'ORAdal' (France Plant Breeders Rights grant number 11682) by the following combination of characteristics:

1. The flowers of 'GRAosr' exhibit distinct strong red petals with yellow at the base and a silvered white reverse, whereas the flowers of 'ORAdal' are uniform crimson red.
2. Growth of 'GRAosr' is upright with bushy growth and clustered flowers, whereas 'ORAdal' is upright with solitary flowers.

That which is claimed:

1. A new and distinct variety of *Rosa* hybrid plant named 'GRAosr', as described and illustrated herein.

* * * * *